United States Patent [19]
Rivett et al.

[11] Patent Number: 5,910,322
[45] Date of Patent: Jun. 8, 1999

[54] DELAYED RELEASE PHARMACEUTICAL FORMULATION CONTAINING AMOXYCILLIN AND POTASSIUM CLAVULANATE

[75] Inventors: Ernest Lionel Gilbert Rivett, Arundel; Francis Walter Grimmett, Rustington; Michael William Hartnell, Worthing, all of United Kingdom

[73] Assignee: SmithKline Beecham p.l.c., United Kingdom

[21] Appl. No.: 08/776,909

[22] PCT Filed: Aug. 8, 1995

[86] PCT No.: PCT/EP95/03151

§ 371 Date: Oct. 2, 1997

§ 102(e) Date: Oct. 2, 1997

[87] PCT Pub. No.: WO96/04908

PCT Pub. Date: Feb. 22, 1996

[30] Foreign Application Priority Data

Aug. 17, 1994 [GB] United Kingdom .................... 9416600

[51] Int. Cl.$^6$ ...................................................... A61K 9/26
[52] U.S. Cl. .......................... 424/484; 424/464; 424/469; 424/470; 424/486; 424/487; 424/489; 424/490; 514/964; 514/965

[58] Field of Search ...................................... 424/484, 486, 424/487, 489, 490, 464, 469, 470; 514/964, 965

[56] References Cited

U.S. PATENT DOCUMENTS 4,173,626  11/1979  Demski et al. .
4,223,006  9/1980  Taskis .

FOREIGN PATENT DOCUMENTS

92/19227  11/1992  WIPO .
94/27557  11/1992  WIPO .
94/06416  3/1994  WIPO .
95/20946  8/1995  WIPO .

*Primary Examiner*—Thurman K. Page
*Assistant Examiner*—Brian K. Seidleck
*Attorney, Agent, or Firm*—Janice E. Williams; Charles M. Kinzig

[57] ABSTRACT

Pharmaceutical formulations for oral administration, comprising a matrix which comprises a β-lactam antibiotic optionally in combination with a β-lactamase inhibitor, granules in a delayed release form dispersed within the matrix, which comprise a β-lactam antibiotic optionally in combination with a β-lactamase inhibitor, the overall tablet formulation including a β-lactam antibiotic and a β-lactamase inhibitor.

11 Claims, No Drawings

DELAYED RELEASE PHARMACEUTICAL FORMULATION CONTAINING AMOXYCILLIN AND POTASSIUM CLAVULANATE

This application claims benefit of U.K. application number 9416600.6 filed Aug. 17, 1994.

This invention relates to pharmaceutical formulations for oral administration, comprising an antibiotic and a β-lactamase inhibitor.

Oral formulations of this type are known, but generally need to be administered three times daily. It is desirable to produce such a formulation in a delayed or sustained release form which may be suitable for less frequent administration. A particularly effective β-lactamase inhibitor is the known compound clavulanic acid and its derivatives (hereinafter collectively termed "clavulanate" unless otherwise specifically identified), especially the potassium salt of clavulanic acid.

The invention therefore provides a pharmaceutical tablet formulation, comprising:

a matrix which comprises a β-lactam antibiotic optionally in combination with a β-lactamase inhibitor, and dispersed within said matrix, granules in a delayed release form ("delayed release granules") which comprise a β-lactam antibiotic optionally in combination with a β-lactamase inhibitor, the overall tablet formulation including a β-lactam antibiotic and a β-lactamase inhibitor.

The matrix preferably includes a β-lactamase inhibitor.

The granules may optionally also include a β-lactamase inhibitor in combination with the β-lactam antibiotic.

The matrix may also include dispersed within it granules ("rapid release granules"), in a form which release their content more rapidly than the delayed-release granules, which comprise a β-lactam antibiotic, optionally in combination with a β-lactamase inhibitor.

Preferred β-lactam antibiotics are penicillins and cephalosporins, in particular amoxycillin, for example in the form of amoxycillin trihydrate. A preferred β-lactamase inhibitor is clavulanate, particularly potassium clavulanate. In the matrix and those granules which contain a β-lactamase inhibitor the ratio antibiotic:β-lactamase inhibitor may vary independently between wide limits, in the case of amoxycillin:clavulanate for example varying between 1:1 to 30:1, for example amoxycillin:clavulanate between 1:1 to 12:1, e.g 2:1, 3:1, 4:1, 5:1, 6:1, 7:1 or 8:1 inclusive expressed as the equivalent weight ratios of the parent free acids. In the overall tablet formulation the ratio antibiotic:β-lactamase inhibitor may also vary between similarly broad limits, for example between: 1 to 30:1, for example between: 1 to 12:1, e.g 2:1, 3:1, 4:1, 5:1, 6:1, 7:1 or 8:1 inclusive.

The matrix may suitably comprise a mixture of amoxycillin and potassium clavulanate in a ratio amoxycillin:clavulanate between 2:1 to 8:1, for example between 2:1 and 4:1 inclusive.

In one form of the tablet formulation of the invention, the tablet has a matrix which comprises amoxycillin and clavulanate, dispersed within which are delayed release granules which comprise amoxycillin and clavulanate. These granules may suitably comprise amoxycillin and potassium clavulanate in a ratio amoxycillin:clavulanate between 2:1 to 8:1 inclusive, for example around 4:1+10%.

In this first form of the tablet the overall distribution of the antibiotic and β-lactamase inhibitor between the matrix:granules may independently suitably vary between 2.5:1 to 1:2.5. Suitably the distribution of matrix amoxycillin:granule amoxycillin is around 1:1.5+10%, and the distribution of matrix clavulanate:granule clavulanate is around 1.5:1+10%.

In a second form of the tablet formulation of the invention, the tablet has a matrix which comprises amoxycillin and clavulanate, dispersed within which are delayed release granules which comprise amoxycillin, and rapid release granules which comprise amoxycillin.

In this second form of the tablet the overall distribution of the amoxycillin between the matrix plus rapid release granules:delayed release granules may vary between 2.5:1 and 1:2.5. Suitably the distribution may be around 1:1.5+10%. Suitably the distribution of amoxycillin between rapid release granules:matrix:delayed release granules may be around 1:1–2:2–6.

The matrix may comprise a compact of compressed ingredients including the antibiotic and optionally present β-lactamase inhibitor. In addition to antibiotic and optionally present β-lactamase inhibitor the matrix may contain conventional additives. Appropriate additives in such a tablet may comprise diluents such as calcium carbonate, magnesium carbonate, dicalcium phosphate or mixtures thereof, binders such as hydroxypropyl-methylcellulose, hydroxypropylcellulose, polyvinylpyrrolidone, pregelatinised starch or gum acacia or mixtures thereof, disintegrants such as cross-linked polyvinylpyrrolidone, sodium starch glycollate, croscarmellose sodium or mixtures thereof, lubricants, such as magnesium stearate or stearic acid, glidants or flow aids, such as colloidal silica, talc or starch, and stabilisers such as desiccating amorphous silica, colouring agents, flavours etc..

The granules may be made by a conventional granulating process as known in the art. Preferably the granules are made by a procedure of dry granulation of the granule components, for example slugging then milling, or by roller compaction then milling. The granules may include conventional additives introduced as a result of the granulation process, e.g. lubricants such as magnesium stearate, in conventional quantities, e.g. ca. 0.5–1 wt % of magnesium stearate. Suitably the granules are of 10–40 mesh size, for example 16–30 mesh size.

To form delayed release granules, the granules are preferably coated with a coating layer of a dissolution-retarding coating. In their uncoated form such granules are rapid release granules, which release their content more rapidly than coated granules. The dissolution-retarding coating may be a polymeric material, for example an enteric polymer (the term "enteric polymer" is a term of the art referring to a polymer which is preferentially soluble in the less acid environment of the intestine relative to the more acid environment of the stomach).

An enteric coating may be an essentially conventional coating material known for enteric coating of antibiotic granules, for example enteric polymers such as cellulose acetate phthalate, cellulose acetate succinate, methylcellulose phthalate, ethylhydroxycellulose phthalate, polyvinylacetate phthalate, polyvinylbutyrate acetate, vinyl acetate-maleic anhydride copolymer, styrene-maleic mono-ester copolymer, methyl acrylate-methacrylic acid copolymer, methacrylate-methacrylic acid-octyl acrylate copolymer, etc. These may be used either alone or in combination, or together with other polymers than those mentioned above. The enteric coating may also include insoluble substances which are neither decomposed nor solubilized in living bodies, such as alkyl cellulose derivatives such as ethyl cellulose, crosslinked polymers such as styrene-divinylbenzene copolymer, polysaccharides having hydroxyl groups such as dextran, cellulose derivatives which are treated with bifunctional crosslinking agents such as epichlorohydrin, dichlorohydrin, 1,2-, 3,4- diepoxybutane, etc. The enteric coating may also include starch and/or dextrin.

Preferred enteric coating materials are the commercially available "Eudragit" (Trade Mark) enteric polymers, such as "Eudragit L" (Trade Mark), "Eudragit S" (Trade Mark) and "Eudragit NE" (Trade Mark) used either alone or with a plasticiser. Such coatings are normally applied using a liquid medium, and the nature of the plasticiser, depends upon whether the medium is aqueous or non-aqueous. Aqueous plasticisers include propylene glycol or "Citroflex" or Citroflex A2" (Trade Marks) (mainly triethyl citrate or acetyl triethyl citrate). Nonaqueous plasticers include these, and also diethyl and dibutyl phthalate and dibutyl sebacate.

The quantity of plasticiser included will be apparent to those skilled in the art. The enteric coating may also include an anti-tack agent such as talc, silica or glyceryl monostearate. The quantity of plasticiser and anti-tack agent may be generally conventional to the art. Typically the coating may include around 10–25 wt. % plasticiser and up to around 50 wt % of anti tack agent, e.g. 5–20 wt. % of anti-tack agent.

The enteric coating may be applied to the granules by dissolving or suspending the enteric coating materials in a suitable medium, such as water, methanol, ethanol, isopropanol, acetone, methyl ethyl ketone, methylene chloride, ethylene chloride, ethyl acetate, etc. or mixtures thereof, and the resultant solution or suspension may be sprayed on the granules to coat them, followed by drying sufficiently with an air flow and screening.

In the case of the preferred enteric coating material referred to above, the enteric coating material may be dissolved or suspended in a solvent for example water and coated onto the granules using a fluidised bed system. If water is used, preferably an anti-foaming agent such as activated polymethylsiloxane is also included.

The dissolution-retarding coating layer may be applied sequentially to the granules, in a batch or continuous process. In a batch process the granules may be removed from the equipment being used to apply the surrounding layer and coated later. In a continuous process, after the surrounding layer had been deposited on the granules the nature of the coating solution may be changed after application of a suitable quantity of the surrounding layer.

Suitably the dissolution-retarding, e.g enteric polymer, coating layer may comprise 15–30 wt. % of the overall granule weight.

The tablet formulation of the invention provides a sustained or delayed release effect following oral ingestion, as the antibiotic and optionally present β-lactamase inhibitor in the matrix, and rapid release granules (when present) are relatively rapidly released in the stomach, whilst the antibiotic and β-lactamase inhibitor in the delayed release granules are relatively slowly released, for example in the intestine as an enteric coating on the granules dissolves preferentially in the more alkaline environment of the intestine.

Methods of compacting matrix materials and granules to form a tablet of the invention are well known in the art. For example the matrix material in a powdered or granulated form and the granules may be screened and blended, and the mixture may then be compressed into a tablet in a conventional manner, e.g in a tabletting press. Some loss of integrity of the granule structure, e.g crushing of the granules, or disruption of a dissolution-retarding coating layer may occur during compaction but this may be reduced by the use of known compaction aids such as starch and/or microcrystalline celluloses. Tablets containing such crushed granules are included within the scope of this invention.

The invention therefore also provides a method of preparing a pharmaceutical formulation as described herein, comprising the steps of forming a matrix which comprises a β-lactam antibiotic optionally in combination with a β-lactamase inhibitor, and dispersed within said matrix, delayed release granules which comprise a β-lactam antibiotic optionally in combination with a β-lactamase inhibitor, the overall tablet formulation including a β-lactam antibiotic and a β-lactamase inhibitor.

The above-mentioned formulations for oral administration may contain quantities of antibiotic and β-lactamase inhibitor up to the maximum amount allowed by regulatory authorities. For example in the case of amoxycillin and clavulanate the total amount of amoxycillin may be 875±100 mg (expressed as the parent free acids), and of clavulanate 250 mg for a daily dose, divided up between one or more unit dosage forms. Unit dosage forms of the tablet of the invention may for example contain nominally 250, 500 or 750 mg of amoxycillin, and a quantity of potassium clavulanate corresponding to the above-mentioned weight ratios of clavulanate.

Clavulanic acid and its derivatives, e.g. salts such as potassium clavulanate are extremely moisture sensitive, and all operations carried out to prepare granules and formulations of this invention which contain clavulanate should be carried out under conditions of low relative humidity, e.g. less than 30% RH.

The present invention also provides a pharmaceutical formulation as described herein for use as an active therapeutic substance.

The present invention also provides a pharmaceutical formulation as described herein for use in the treatment of bacterial infections.

The present invention also provides the use of a formulation as described herein in the manufacture of a medicament for use in the treatment of bacterial infections.

The present invention also provides a method of treatment of bacterial infections in humans or animals which comprises the administration of an effective amount of a pharmaceutical formulation as described herein.

The invention will now be described by way of example only.

EXAMPLE 1

A tablet formulation comprising a matrix within which are dispersed delayed release granules of amoxycillin trihydrate in combination with potassium clavulanate.

Granules.

Granules were prepared by roller compaction of an amoxycillin trihydrate:potassium clavulanate 4:1 ww mix blended with 0.5% magnesium stearate. This mix is fed to a Fitzpatrick Chilsonator, with a Fitzmill under the compactor and then a multiple deck sieve under the mill. The compacted flake generated at 1000 psi pressure is fed through the mill, fitted with an 0.074" aperture screen operating at a speed 2000 rpm, with knives forward. The milled granule is fed to a multideck sieve, fitted with a 1000 micron sieve, overlaying a 500 micron sieve overlying a 180 micron sieve. Fractions larger than 1000 microns and less than 180 microns are recycled. Fractions passing a 1000 micron sieve and retained on a 500 micron sieve are collected for coating.

Coating.

| Component | % ww |
|---|---|
| Granules from roller compaction | 65.00 |
| Eudragit L30D | 23.10 |
| Eudragit NE30D Ph. Eur | 5.79 |
| Talc USP/Ph. Eur | 5.79 |
| Antifoam M | 0.32 |
| Purified Water Ph. Eur | qs* |
| Total | 100.00 |

* removed during processing.

The granules are coated with a Eudragit L30D/Eudragit NE30D suspension in a fluidised bed to produce delayed release granules.

Tabletting.

| Component | % ww |
|---|---|
| Amox. (H₂O)₃:Pot. Clav. 1:1 blend(matrix) | 6.25 |
| Amoxycillin trihydrate (matrix) | 7.50 |
| Coated granules | 33.78 |
| Magnesium Stearate Ph. Eur or NF | 0.50 |
| Microcrystalline cellulose BP or NF] (Avicel PH 112)      ] | q.s.* |
| Calcium carbonate granules** | q.s.* |
| Total | 100.00 |

* these two excipients are used as a 60:40 blend in a quantity to total 100%.
** prepared as in example 2 below.

The components are screened and blended, and compressed to form oval tablets 19.0×9.0 mm, nominal weight 1000 mg. The formulation contains a 100/150 mg split between rapid and delayed release amoxycillin and a 25/37.5 mg split between rapid and delayed release clavulanate.

EXAMPLE 2

A tablet formulation comprising a matrix of amoxycillin trihydrate and clavulanate in combination, with rapid release and delayed release amoxycillin granules dispersed within the matrix.

Rapid-release amoxycillin granules.

| Component | wt. % |
|---|---|
| Amoxycillin trihydrate BP | 99.5 |
| Magnesium stearate Ph. Eur. | 0.5 |
| Total | 100.00 |

Granules are prepared by slugging the dry blend of components, and reducing the slugs through an Apex mill. The granules are sieved to produce 16–30 mesh material. These granules were used to prepare delayed release amoxycillin granules as below.

Delayed-release amoxycillin granules.

| Component | wt. % |
|---|---|
| Rapid release amoxycillin granules | 75.0 |
| Eudragit L30D USP | 19.53 |
| Propylene glycol Ph. Eur | 3.14 |
| Talc Ph. Eur. | 2.07 |
| Antifoam M | 0.26 |
| Purified water Ph. Eur | q.s.* |
| Total | 100.00 |

* removed during processing.

The rapid release amoxycillin granules are coated with Eudragit L30D coating in a fluidised bed coater.

Calcium carbonate granules.

| Component | wt. % |
|---|---|
| Calcium carbonate (Sturcal F) | 96.0 |
| Polyvinyl pyrollidone (Kollidon 25) | 4.0 |
| Water BP | q.s.* |
| Total | 100.00 |

* removed during processing.

The calcium carbonate is wet massed with polyvinyl pyrollidone dissolved in water. The mass is broken through a No. 12 mesh sieve prior to drying at 100° C. in a forced air oven. The dry granules are then passed through a No. 30 mesh sieve.

Tabletting.

| Component | wt. % |
|---|---|
| Amox. (H₂O)₃:Pot. Clav. 1:1 blend(matrix) | 28.41 |
| Rapid release amoxycillin granules | 8.01 |
| Delayed release amoxycillin granules | 42.55 |
| Magnesium stearate Ph. Eur or NF | 0.50 |
| Microcrystalline cellulose BP or NF] (Avicel PH 112)      ] | q.s.* |
| Calcium carbonate granules | q.s* |
| Total compression mix weight | 100.00 |

* These excipients are present in the ratio of 60:40 and a quantity taken sufficient to a total of 100%.

The components are screened and blended, and compressed to prepare oval tablets, 19.0×9.0 mm, nominal weight 1100 mg. The formulation provides a 200/300 mg split between rapid (matrix+granules) and delayed (granules) release amoxycillin and 125 mg rapid release matrix potassium clavulanate.

We claim:

1. A pharmaceutical tablet formulation, comprising: a matrix which comprises a β-lactam antibiotic and a β-lactamase inhibitor, and dispersed within said matrix granules in a delayed-release form which comprise a β-lactam antibiotic and a β-lactamase inhibitor, and dispersed within said matrix granules in a rapid-release form which comprise a β-lactam antibiotic and a β-lactamase inhibitor.

2. A formulation according to claim 1 which the matrix includes dispersed within it granules in a rapid-release form which release their content more rapidly than the granules in a delayed-release form.

3. A formulation according to claim 1 in which the β-lactam antibiotic is amoxycillin.

4. A formulation according to claim 1 wherein the β-lactamase inhibitor is clavulanate.

5. A tablet formulation according to claim 1 in which the tablet has a matrix which comprises amoxycillin and clavulanate, dispersed within which are delayed release granules which comprise amoxycillin and clavulanate.

6. A tablet formulation according to claim 1 in which the tablet has a matrix which comprises amoxycillin and clavulanate, dispersed within which are delayed release granules which comprise amoxycillin and clavulanate, and rapid release granules which comprise amoxycillin and clavulanate.

7. A tablet formulation according to claim 5 in which the overall distribution of the amoxycillin between the matrix plus rapid release granules:delayed release granules may vary between 2.5:1 and 1:2.5.

8. A tablet formulation according to claim 1 in which the matrix comprises a compact of compressed ingredients including the β-lactam antibiotic and a β-lactamase inhibitor.

9. A tablet formulation according to claim 1 wherein the delayed release granules are coated with a coating layer of a dissolution-retarding coating.

10. A method of preparing a pharmaceutical formulation according to of the claim 17, comprising the steps of forming a matrix which comprises a β-lactam antibiotic a β-lactamase inhibitor, and dispersed within said matrix, delayed release granules which comprise a β-lactam antibiotic a β-lactamase inhibitor, the overall tablet formulation including a β-lactam antibiotic and a β-lactamase inhibitor.

11. A method of treatment of bacterial infections in humans or animals which comprises the administration of an effective amount of a pharmaceutical formulation according to claim 1.

* * * * *